United States Patent
Zhang

(10) Patent No.: US 8,442,624 B2
(45) Date of Patent: May 14, 2013

(54) SYSTEM FOR CARDIAC MEDICAL CONDITION DETECTION

(75) Inventor: Hongxuan Zhang, Palatine, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 189 days.

(21) Appl. No.: 12/986,205

(22) Filed: Jan. 7, 2011

(65) Prior Publication Data
US 2011/0282227 A1   Nov. 17, 2011

Related U.S. Application Data

(60) Provisional application No. 61/333,773, filed on May 12, 2010.

(51) Int. Cl.
  *A61B 5/04*    (2006.01)
  *A61N 1/00*    (2006.01)
(52) U.S. Cl.
  USPC .......... 600/509; 600/516; 600/517; 600/521; 607/25
(58) Field of Classification Search .............. 600/509, 600/516, 517, 521; 607/25
  See application file for complete search history.

(56) References Cited

U.S. PATENT DOCUMENTS

| | | | |
|---|---|---|---|
| 5,549,641 A | 8/1996 | Ayers et al. | |
| 5,683,429 A | 11/1997 | Mehra | |
| 5,788,717 A | 8/1998 | Mann et al. | |
| 5,968,079 A | 10/1999 | Warman et al. | |
| 6,064,906 A | 5/2000 | Langberg et al. | |
| 6,070,097 A * | 5/2000 | Kreger et al. | 600/521 |
| 6,263,244 B1 | 7/2001 | Mann et al. | |
| 6,285,908 B1 | 9/2001 | Mann et al. | |
| 6,490,479 B2 | 12/2002 | Bock | |
| 6,597,943 B2 | 7/2003 | Taha et al. | |
| 6,618,622 B1 | 9/2003 | Mann et al. | |
| 6,738,655 B1 | 5/2004 | Sen et al. | |
| 6,968,226 B2 | 11/2005 | Mehra | |
| 7,092,751 B2 | 8/2006 | Erkkila | |
| 7,117,029 B2 | 10/2006 | Stridh et al. | |
| 7,153,301 B2 | 12/2006 | Swartz et al. | |
| 7,177,682 B2 | 2/2007 | Lovett | |

(Continued)

OTHER PUBLICATIONS

Joao Tranchesi M.D.; Victor Adelardi M.D.; Jorge Martins De Oliveira M.D., "Atrial Repolarization—Its Importance in Clinical Electrocardiography", Circulation, 1960; vol. 22, p. 635-644.

(Continued)

*Primary Examiner* — Niketa Patel
*Assistant Examiner* — Rimi Sahu
(74) *Attorney, Agent, or Firm* — Alexander J Burke

(57) ABSTRACT

A system for heart performance characterization and abnormality detection processes a heart electrical activity signal in determining multiple first signal characteristic values over multiple heart cycles. A first signal characteristic value substantially comprises a time interval between a peak of a P wave to a peak of a succeeding R wave representing a repolarization time interval in an individual heart cycle and the signal processor uses a peak detector and time detector for identifying the peaks and detecting a time difference between the identified peaks. A comparator compares at least one of the multiple first signal characteristic values or a value derived from the multiple first signal characteristic values with a threshold value to provide a comparison indicator. A patient monitor in response to the comparison indicator indicating a calculated signal characteristic value exceeds the threshold value, generates an alert message associated with the threshold.

26 Claims, 10 Drawing Sheets

U.S. PATENT DOCUMENTS

| | | | |
|---|---|---|---|
| 7,321,794 | B2 | 1/2008 | Thacker |
| 7,328,066 | B1 | 2/2008 | Levine |
| 7,343,197 | B2* | 3/2008 | Shusterman ............... 600/509 |
| 7,627,368 | B2 | 12/2009 | Houben et al. |
| 7,634,310 | B2 | 12/2009 | Lee et al. |
| 7,643,878 | B1 | 1/2010 | Muller et al. |
| 2007/0239214 | A1* | 10/2007 | Cinbis ............................. 607/5 |
| 2009/0005828 | A1* | 1/2009 | Levine ........................... 607/14 |

OTHER PUBLICATIONS

F Jousset1, JM Vesin1, P Pascale2, P Ruchat2, S C Schaefer2, M Fromer2, E Pruvot, "In Vivo Measurements of Atrial Repolarization Alternans Based on Standard Pacemaker Technology", Computers in Cardiology, 2009; vol. 36, p. 145-148.

P Langley, M Stridh, JJ Rieta, L Sörnmo, J Millet-Roig, A Murray, "Comparison of Atrial Rhythm Extraction Techniques for the Estimation of the Main Atrial Frequency from the 12-lead Electrocardiogram in Atrial Fibrillation", Computers in Cardiology, 2002, vol. 29, p. 29-32.

Gang Wang, Ni-ni Rao, Simon J. Shepherd, and Clive B. Beggs, "Extraction of Desired Signal Based on AR Model with Its Application to Atrial Activity Estimation in Atrial Fibrillation", EURASIP Journal on Advances in Signal Processing, vol. 2008 (2008), Article ID 728409, 9 Pages.

Martin Stridh, Andreas Bollmann, S.Bertil Olsson, and Leif Sörnmo, "Detection and Feature Extraction of Atrial Tachyarrhythmias, A three stage method of time-frequency analysis ", IEEE Engineering in Medicine and Biology Magazine, Nov.-Dec. 2006, vol. 25, No. 6, p. 31-9.

José Joaquin Rieta, Francisco Castells, César Sánchez, Vicente Zarzoso, and José Millet, "Atrial Activity Extraction for Atrial Fibrillation Analysis Using Blind Source Separation", IEEE Transactions on Biomedical Engineering, vol. 51, No. 7, Jul. 2004, p. 1176-1186.

\* cited by examiner

| Signal | Cardiac function | Calculation |
|---|---|---|
| Depolarization timing | To detect variation and variability of atrial Depolarization | Mean value: $Mean(T_D)$<br>Standard deviation: $STD(T_D)$<br>Variation: $Mean(T_D)/STD(T_D)$ (#1) |
| Repolarization timing | To detect variation and variability of atrial Repolarization | Mean value: $Mean(T_R)$<br>Standard deviation: $STD(T_R)$<br>Variation: $Mean(T_R)/STD(T_R)$ |
| PQ timing | To detect variation and variability of Q wave delay due to atrial Repolarization variation | Mean value: $Mean(T_{PQ})$<br>Standard deviation: $STD(T_{PQ})$<br>Variation: $Mean(T_{PQ})/STD(T_{PQ})$ |
| QR timing | To detect variation and variability of R wave delay due to atrial Repolarization variation | Mean value: $Mean(T_{QR})$<br>Standard deviation: $STD(T_{QR})$<br>Variation: $Mean(T_{QR})/STD(T_{QR})$ |
| Ratio of depolarization to repolarization | To detect variation and variability of atrial function and pathology (depolarization vs. repolarization) | Mean value: $Mean(Ratio_{D-R})$<br>Standard deviation: $STD(Ratio_{D-R})$<br>Variation: $Mean(Ratio_{D-R})/STD(Ratio_{D-R})$ |
| Other timing ratio_1 | To detect variation and variability of atrial function and pathology | Mean value: $Mean(Ratio_{D-Q})$<br>Standard deviation: $STD(Ratio_{D-Q})$<br>Variation: $Mean(Ratio_{D-Q})/STD(Ratio_{D-Q})$ |
| Other timing ratio_2 | To detect variation and variability of atrial function and pathology (signal distribution changes within the atrial repolarization portion) | Mean value: $Mean(Ratio_{P-R})$<br>Standard deviation: $STD(Ratio_{P-R})$<br>Variation: $Mean(Ratio_{P-R})/STD(Ratio_{P-R})$ |

SYSTEM FOR CARDIAC MEDICAL CONDITION DETECTION

This is a non-provisional application of provisional application Ser. No. 61/333,773 filed May 12, 2010, by H. Zhang.

FIELD OF THE INVENTION

This invention concerns a system for heart performance characterization and abnormality detection, by determining and characterizing peak to peak time intervals within a heart activity representative signal, for example.

BACKGROUND OF THE INVENTION

Atrial arrhythmia, such as Atrial Fibrillation (AF), is a common cardiac arrhythmia which may contribute to significant risks of electrophysiological disorders, leading to morbidity and mortality, as well as thrombo-embolism and stroke. Atrial arrhythmia, such as AF, is a common cardiac pathology in the older population, and is an irregularity of the heart rhythm. Instead of only one area in the atrium initiating an electrical signal, multiple different areas generate electrical signals. A complex of electrical impulses or wavelets spreads over atrial tissue and causes an atrial muscle to quiver or fibrillate, rather than contracting in an organized way. Some of the electrical impulses still travel down through the heart and make the bottom chambers squeeze or contract. The irregularity of the impulses traveling down from the atria makes the ventricles beat irregularly, so a pulse may feel irregular. Sometimes AF can make the pulse fast and irregular or slow and irregular. A heart in atrial fibrillation does not beat efficiently. It may not be able to pump enough blood into a body with each heartbeat. Due to the insufficient blood flow, the heart may drastically increase the heart rate. For example the heart rate in atrial fibrillation may range from 100 to 175 beats per minute. The normal range for a heart rate is 60 to 100 beats per minute.

AF alone is not a life-threatening arrhythmia, but it can be extremely bothersome and sometimes dangerous. For example, in atrial fibrillation, the chaotic rhythm may cause blood to pool in an atria and form clots. If a blood clot forms, it may dislodge and travel to the brain and block blood flow, causing a stroke. The risk of stroke in atrial fibrillation depends on age and blood pressure, diabetes, or a history of heart failure or previous stroke, and other factors. Atrial fibrillation can be paroxysmal (episodes come and go on their on), persistent (episodes come and last until rhythm is re-established) or permanent (the heart stays in AF despite efforts to convert to a normal rhythm). There may be many causes and factors which may induce atrial fibrillation, such as high blood pressure, atrial or valve abnormality, alcohol and family history. Early detection of atrial arrhythmia helps to reduce risk and discomfort and facilitates bringing a heart back to normal heart rhythm using an energy based cardioverter electrical shock, for example. Known waveform morphologies and time domain parameter analysis of atrial arrhythmia focus on P wave analysis which concerns the depolarization procedure of the atrium. P wave changes (atrial depolarization signals) alone may not be able to provide early detection of atrial pathologies.

Known analysis based on P wave morphology changes fails to differentiate atrial arrhythmia type and categorize severity of atrial arrhythmia. Further known methods for complex cardiac atrial arrhythmia identification and diagnosis using a surface ECG signal are subjective and need extensive expertise for accurate interpretation and appropriate cardiac rhythm management. This is particularly the case in the early stage of the atrial fibrillation in which the P wave morphology distortion and changes are small and atrial arrhythmias are not easy to detect. Known atrial arrhythmia (such as fibrillation) detection methods include heart rate variability detection. However the efficiency and reliability of known clinical approaches is often inadequate, especially in a noisy environment since atrial activities may be buried in noise. In known clinical applications, atrial arrhythmia diagnosis and treatment, especially in an early stage, are typically heavily dependent on physician experience. A system according to invention principles addresses these deficiencies and related problems.

SUMMARY OF THE INVENTION

A system improves characterization and interpretation of cardiac atrial electrophysiological activities by processing atrial depolarization and repolarization activity data involving P wave, PQ wave and QR wave data, for example. A system for heart performance characterization and abnormality detection includes an interface for receiving sampled data representing an electrical signal indicating electrical activity of a patient heart over multiple heart beat cycles. A signal processor uses the received sampled data in determining multiple first signal characteristic values over multiple heart cycles. A first signal characteristic value substantially comprises a time interval between a peak of a P wave to a peak of a succeeding R wave representing a repolarization time interval in an individual heart cycle and the signal processor uses a peak detector and time detector for identifying the peaks and detecting a time difference between the identified peaks. A comparator compares at least one of the multiple first signal characteristic values or a value derived from the multiple first signal characteristic values with a threshold value to provide a comparison indicator. A patient monitor in response to the comparison indicator indicating a calculated signal characteristic value exceeds the threshold value, generates an alert message associated with the threshold.

BRIEF DESCRIPTION OF THE DRAWING

FIG. 4 shows a table identifying type of atrial activity and functions used for time duration and ratio based atrial arrhythmia detection, according to invention principles.

DETAILED DESCRIPTION OF THE INVENTION

A system improves interpretation of cardiac atrial electrophysiological activities, by processing atrial electrophysiological signals (including surface ECG signals and intracardiac electrograms) and analyzing atrial depolarization and repolarization activity, involving a P wave, PQ wave and QR wave, for example. The system quantifies signal waveform changes and distortion within atrial electrophysiological signals, especially atrial repolarization, to provide an accurate time and severity of atrial pathologies and events for improved diagnosis, such as of AF arrhythmia. The system performs cardiac atrial repolarization electrophysiological activity analysis for atrial arrhythmia (especially AF) and function characterization. Cardiac tissue is typically affected by occurrence of certain abnormality or clinical events and the cardiac pacing and excitation conduction mechanism is impacted showing nonlinear abnormal variations. This may impact both depolarization and repolarization procedures and electrophysiological signals indicate response and activities of the heart muscle and tissue and reflect pacing excitation and conduction patterns. The system involves atrial arrhythmia signal extraction, analysis and characterization e.g., using TFI (time frequency calculated parameters) for particular clinical applications using multi-channel or single channel catheter signals for automatic Atrial rhythm evaluation and diagnosis for use in an implantable cardioverter-defibrillator (ICD) or other device, for example. Atrial activities may be divided into depolarization and repolarization portions. A clinical application employs depolarization (P wave) data to determine and characterize atrial abnormality and events. However, atrial muscle function and activities are not just exhibited in a P wave and repolarization activities may show effects in a QR wave portion.

Figure 2:
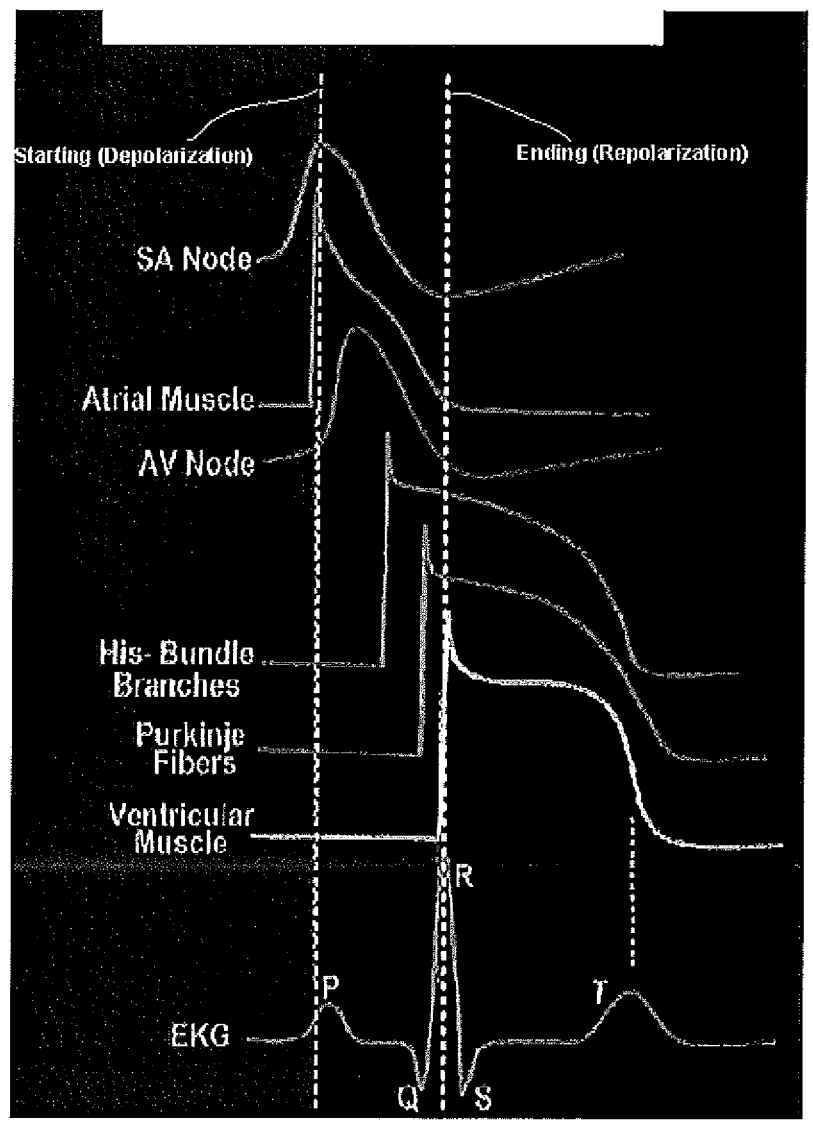
FIG. 2 illustrates electrophysiological signals and responses from different portions of cardiac tissue and chambers which affect EKG/ECG signals.

FIG. 2 illustrates electrophysiological signals and responses from different portions of cardiac tissue and chambers which affect EKG/ECG signals e.g., signal 203. The period of time from the onset of a P wave to the beginning of the QRS complex is termed the P-R interval, which normally ranges from 0.12 to 0.20 seconds in duration. This interval represents the time between the onset of atrial depolarization and the onset of ventricular depolarization. The atrial activities and response signal distribution show the P wave is the depolarization portion of the atrial function. The repolarization is associated with additional information in an ECG signal, such as a PQ portion and QR portion, which comprises about 30-120 ms. Atrial response is typically from early P wave to R wave. Depolarization is a fast wave portion and may not be usable to track and capture small signal changes resulting from early atrial arrhythmias. However in these abnormal cases, such as AF and other pathologies (where multi rotors in the atrium may delay atrial response and impact an ECG signal), the repolarization usually is affected and is easier to monitor via calculation according to invention principles.

Figure 3:
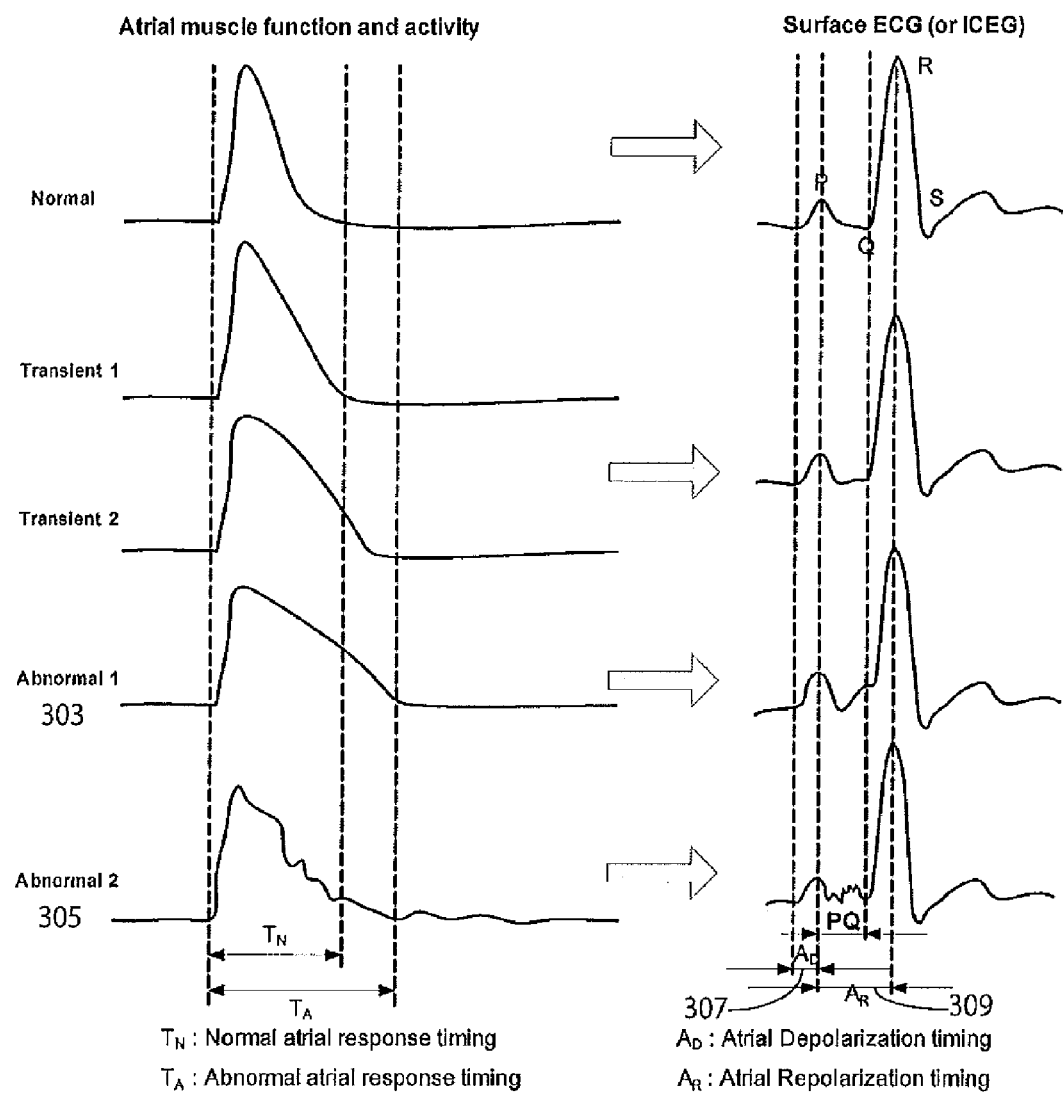
FIG. 3 shows morphology and timing between atrial muscle and ECG signals.

FIG. 3 shows atrial depolarization and repolarization and morphology and time duration between atrial muscle and ECG signals and shows atrial function and electrophysiological response in different cases including normal and abnormal. During abnormal (atrial arrhythmia) cases shown by signals 303, 305, the atrial response is partially delayed and the whole atrial activity time is prolonged. Based on the signal morphology and cardiac tissue response, the system determines atrial depolarization and repolarization. Specifically, an atrial depolarization procedure, $A_D$ 307, comprises a time duration between onset of a P wave to a peak of the P wave. An atrial repolarization procedure, $A_R$ 309 comprises a time duration between a peak of the P wave to a peak of an R wave (the repolarization time may be longer but the repolarization information and energy are mainly associated with the PR portion). Atrial electrical excitation may be delayed and distorted in response to atrial abnormality (such as an atrial conduction problem, atrial arrhythmia or AF). Typically a repolarization procedure is of longer time duration than a depolarization procedure which means a small distortion and change due to atrial arrhythmia may be easier to detect by calculation using parameters associated with a repolarization portion. Additionally, a ratio between atrial depolarization and repolarization facilitates early detection and characterization of distortion and changes within signals and predicts potential risk and need for treatment.

Compared with a normal ECG signal, an abnormal signal due to atrial arrhythmia may have longer repolarization time duration, more high frequency components in the signal morphology, and different ratios between atrial depolarization and repolarization. Atrial repolarization may have a longer time duration than repolarization which facilitates detection of atrial signal distortion and atrial event information.

Figure 1:
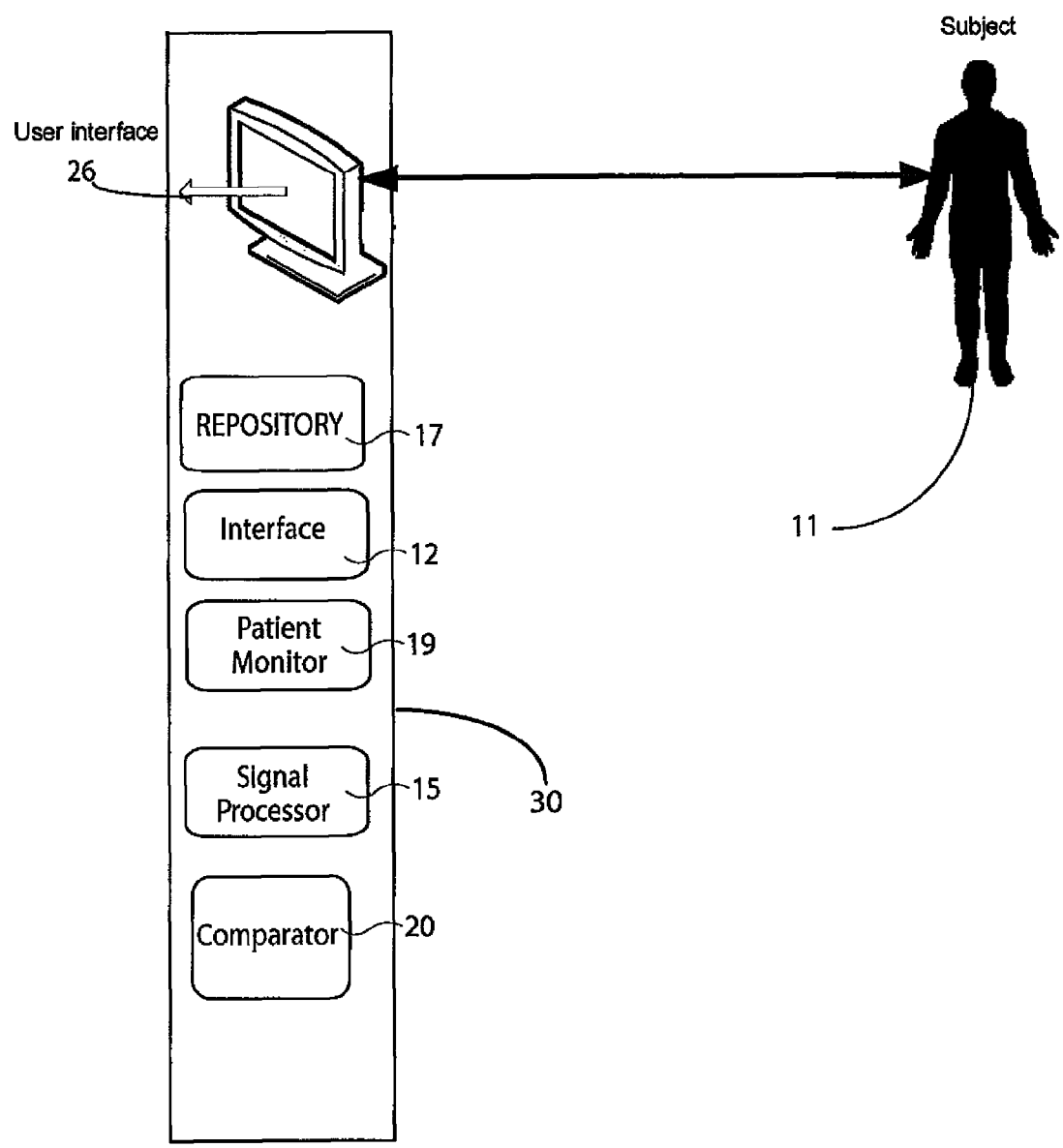
FIG. 1 shows a system for heart performance characterization and abnormality detection, according to invention principles.

FIG. 1 shows system 10 for heart performance characterization and abnormality detection. System 10 comprises at least one computer system, workstation, server or other processing device 30 including interface 12, repository 17, patient monitor 19, signal processor 15, comparator 20 and a user interface 26. Interface 12 receives sampled data representing an electrical signal indicating electrical activity of a patient heart over multiple heart beat cycles. Signal processor 15 uses the received sampled data in determining multiple first signal characteristic values over multiple heart cycles including, a first signal characteristic value substantially comprising a time interval between a peak of a P wave to a peak of a succeeding R wave representing a repolarization time interval in an individual heart cycle. Signal processor 15 uses a peak detector and time detector for identifying the peaks and detecting a time difference between the identified peaks. Comparator 20 compares at least one of the multiple first signal characteristic values or a value derived from the multiple first signal characteristic values with a threshold value to provide a comparison indicator. Patient monitor 19, in response to the comparison indicator indicating a calculated signal characteristic value exceeds the threshold value, generates an alert message associated with the threshold.

FIG. 4 shows a table identifying type of atrial activity and functions used for time duration and ratio based atrial arrhythmia detection. Signal processor 15 uses a peak detector and time detector for identifying peaks and points within the received sampled data including onset of a P wave, for example, and for detecting a time difference between identified peaks. Signal processor 15 determines the time durations and ratios of column 403 including the following, Depolarization time duration, $T_D$=from the onset of a P wave to the peak of a P wave, Repolarization time duration, $T_R$=from the peak of a P wave to the peak of an R wave, PQ time duration, $T_{PQ}$=from the peak of a P wave to the peak of a Q wave; (time change indicates Q wave delay)

QR time duration, $T_{QR}$=from the peak of a Q wave to the peak of an R wave; (time change indicates Q wave distortion), Ratio of depolarization to repolarization, $$Ratio_{D-R} = \frac{T_D}{T_R}$$

Additional ratios, $$Ratio_{D-Q} = \frac{T_D}{T_{PQ}};$$

$$Ratio_{P-R} = \frac{T_{PQ}}{T_{QR}}.$$

Column 405 describes the cardiac functions associated with the corresponding calculated time durations and ratios identified in column 403 that are further analyzed by the corresponding mean, standard deviation and variation functions indicated in column 407.

Signal processor 15 detects peaks of P Q R waves within the received sampled data by synchronization of a heart electrical activity waveform and peak detection of an R wave using a known peak detector and by identifying peaks of other waves by segmenting the signal represented by the sampled data into windows where the waves are expected and identifying the peaks within the windows. The Start point of a P wave, for example, is identified by a variety of known different methods. In one method the P wave start point comprises where the signal crosses a baseline of the signal (in a predetermined P wave window, for example). The baseline of the signal may comprise a zero voltage line if a static (DC) voltage signal component is filtered out from the signal.

Signal processor 15 selects a time frequency integral function for a TFI calculation in response to user direction or adaptive selection by system 10 to reduce impact of noise such as 15 Hz, for instance. The TFI calculation is performed for individual heart cycles (the calculation can be for a single cycle or averaged over several heart cycles). The TFI calculation may be performed for successive individual cycles (intensive monitoring) or at periodic time intervals, such as every 5 seconds, for example. The calculations may employ a multiple heart beat averaging window to obtain mean and standard deviation values of time duration and ratio parameters, for example. The size of the averaging calculation window is adaptively adjusted by the system or a user. A user may employ calculated parameters based on atrial function and variation of depolarization and repolarization. A user may use one or several calculation indices (time duration, ratio) to track and capture atrial function and event information.

Signal processor 15 determines mean or average value (expectation), standard deviation, variation and variability of the calculated time durations and ratios using the following functions.

Mean or average value (expectation), $$mean(X) = \frac{1}{N} \sum_{i \in N} X(i);$$

Standard deviation, $$STD(X) = \frac{1}{N-1} \sum_{i \in N-1} (X(i) - mean(X))$$

$$Signal\ Variation = \frac{mean(X)}{STD(X)}$$

$$Signal\ Variability = \frac{max(X - mean(X))}{mean(X)}$$

where, X is a time duration or ratio determined within an individual heart cycle (beat), N is a calculation window size (there are N heart beats in a shifting calculation window).

Initial change in atrial function due to pathology or an event may be small and buried in a heart activity representative signal in different portions of the heart signal, such as in an atrial repolarization or ventricular depolarization portion. System 10 adaptively employs different methods to extract and capture atrial repolarization signals including time frequency analysis.

Figure 5:
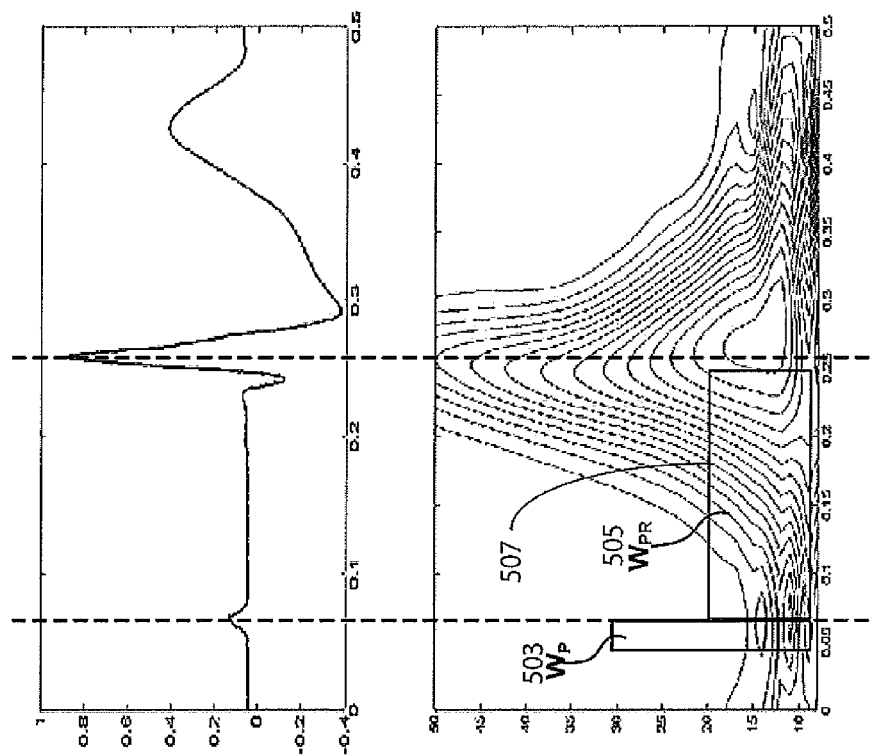
FIG. 5 shows a time-frequency joint signal distribution for a heart cycle indicating cardiac signal activities in both time and frequency domains, according to invention principles.

FIG. 5 shows a time-frequency joint signal distribution for a heart cycle indicating cardiac signal activities in both time and frequency domains over a heart cycle. The joint time-frequency analysis is used to quantify and characterize atrial function, such as by determining an energy related parameter in a pre-selected region of interest (ROI) area comprising a particular time and frequency band such as by determining an energy ratio between atrial depolarization and repolarization heart cycle portions. Atrial repolarization and ventricular depolarization signals overlap in frequency and time which may impact atrial depolarization and repolarization ratio analysis to a limited degree. However in most atrial arrhythmia cases, ventricular depolarization signals and activities are stable and typically do not cause variation and variability in atrial analysis so the contribution or distortion from ventricular depolarization in a time frequency analysis is often reasonably constant in a ratio calculation.

In the time frequency distribution, $W_P$ 503 represents a time-frequency calculation parameter for an atrial depolarization portion in a heart cycle (from onset of a P wave to a Peak of the P wave) and $W_R$ 505 represents a time-frequency calculated parameter for an atrial repolarization procedure (from Peak of the P wave to an R wave). In a PR portion, the atrial repolarization signals may be buried and distorted in a ventricular depolarization portion, especially during a QR portion of the heart cycle signal. The system advantageously extracts atrial repolarization data with a time and frequency band width control (such as $W_{PR}$ window 507). Usually ventricular depolarization signals (i.e., of a QR portion) occupy a higher frequency (10-100 Hz) band and system 10 (FIG. 1) extracts atrial information by selecting and using a lower band width filter (5-25 Hz).

System 10 determines an atrial depolarization time-frequency parameter, $$TFI_{Depolarization} = \int_{t \in T_D; f \in F_D} |x(t, f)|^2$$

where $T_D$ and $F_D$ are the time and frequency bandwidth for an atrial depolarization procedure and x(t, f) is a value for each distribution point in the joint time-frequency analysis in the $T_D$ and $F_D$ ROI area. A user or the system adaptively selects these parameters to improve sensitivity and reliability (especially in a noisy environment). For example $T_D$, from onset of a P wave to Peak of the P wave, is about 15-30 mS, and $F_D$ is selected as 5 Hz to 35 Hz, System 10 determines an atrial repolarization time-frequency parameter, $$TFI_{Repolarization} = \int_{t \in T_R; f \in F_R} |x(t, f)|^2$$

where $T_R$ and $F_R$ are the time and frequency band width for an atrial repolarization procedure and x(t, f) is a value for each distribution point in the joint time frequency analysis in the $T_R$ and $F_R$ ROI area, A user or the system adaptively selects these parameters to improve sensitivity and reliability (especially in a noisy environment). For example $T_D$ (from Peak of the P wave to R wave, is about 30-100 mS) and $F_D$ (from 5 Hz to 20 Hz). System 10 determines an atrial function time-frequency parameter ratio, $$TFI_{Atrial\_fuention\_ratio} = \frac{TFI_{Depolarization}}{TFI_{Repolarization}} = \frac{\int_{t \in T_D; f \in F_D} |x(t, f)|^2}{\int_{t \in T_R; f \in F_R} |x(t, f)|^2};$$

The time-frequency calculated parameters and ratio are used separately and independently in one embodiment to track and monitor atrial function changes and signal distortions. For example, an atrial repolarization time-frequency value and calculated variation and variability of the $TFI_{Repolarization}$ value are used to track small changes in atrial abnormality and pathology. The system 10 calculation uses an averaging window of multiple heart beats to improve SNR and to derive associated mean and standard deviation values, for example. The system 10 calculations provide different ways for analyzing atrial function in different domains, including in the time domain alone or in a joint time-frequency distribution. A calculated parameter value indicates atrial events and is processed to identify type and severity of atrial events by using a calculated value offset from a standard value or reference value (a predefined baseline). The percentage of offset between the real time calculation value and reference baseline indicates severity and is used to predict an atrial event. The calculations may also be used to identify a trend in atrial pathology and drug delivery effects. Additionally the calculations are used in combination to improve detection sensitivity and reliability in real time atrial signal and response monitoring.

The calculations are used for analyzing multi-channel ECG signals and ICEG signals. For example in a basket catheter, there are 64 channel ICEG signals and system 10 employs the described functions to calculate parameters used to analyze the multi-channel signals from different cardiac positions and tissue and to monitor atrial arrhythmia location, severity and arrhythmia types (Atrial fimbriation, atrial flutter). This facilitates determination of medical treatment and tissue location for ablation and priority of tissue areas for ablation, for example. Furthermore, the atrial repolarization signals and calculated electrophysiological response values are used to evaluate and characterize patient health and cardiac function status. In response to data indicating a clinical application (e.g., AF monitoring), a statistical calculation and related hypothesis (such as T test) are selected and utilized for quantification of the stages of the cardiac events and pathologies to identify an event and trend and to determine an associated confidence level in the identification.

Figure 6:
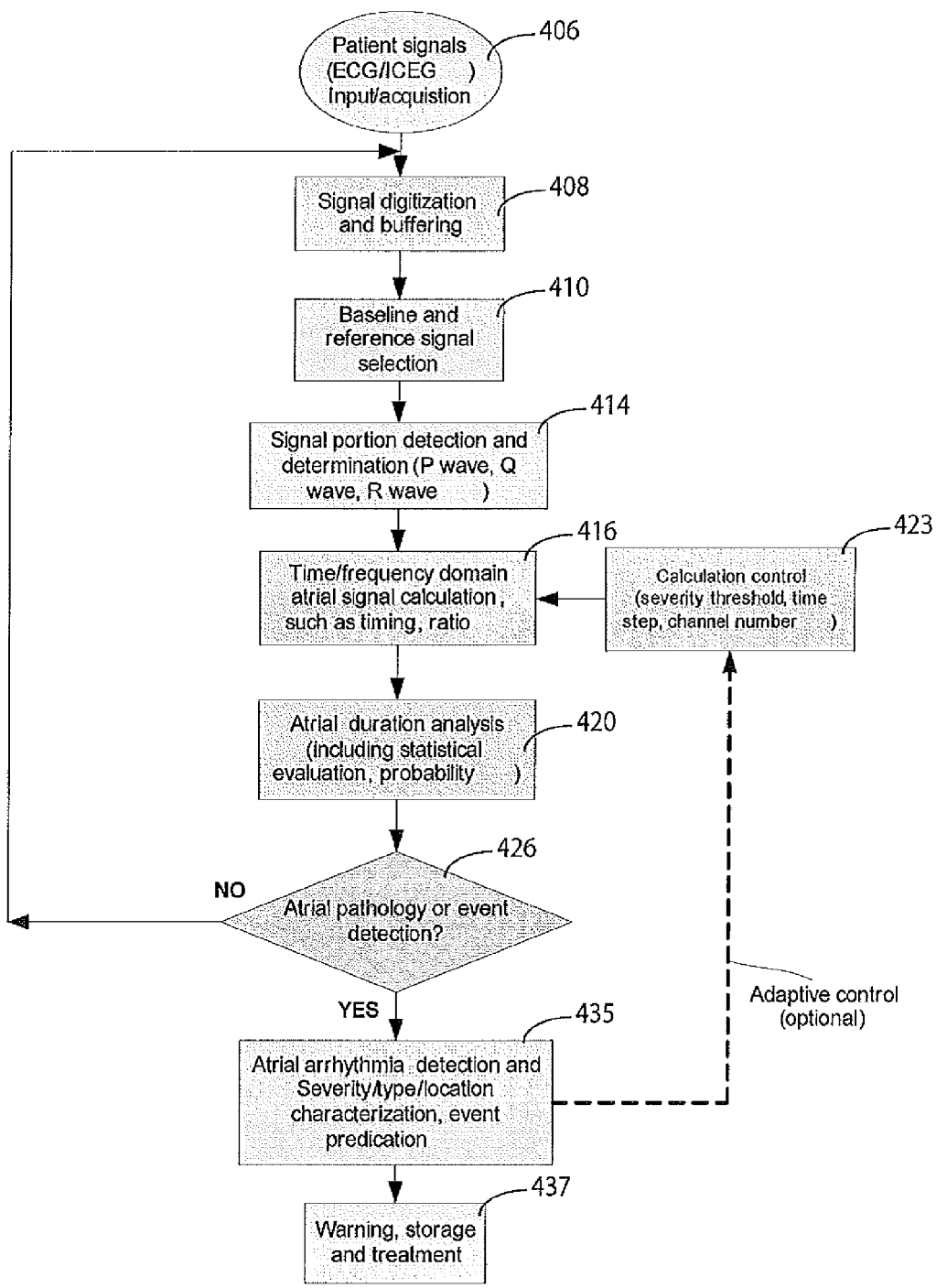
FIG. 6 shows a flowchart of a process performed by the system for atrial repolarization signal analysis for atrial arrhythmia event detection and characterization, according to invention principles.

FIG. 6 shows a flowchart of a process performed by system 10 (FIG. 1) for atrial repolarization signal analysis for atrial arrhythmia event detection and characterization. Interface 12 in step 408 provides sampled heart activity data by buffering and digitizing an electrical signal received in step 406 and indicating electrical activity of a patient heart over multiple heart cycles. Interface 12 filters the sampled data using a filter adaptively selected in response to data indicating clinical application (e.g. ischemia detection, rhythm analysis application) and in step 410 determines a baseline level of the filtered sampled data signal. Interface 12 further selects a previously stored reference sampled data signal for comparison with the filtered sampled data signal. In step 414, signal processor 15 identifies heart cycles and different segments (QRS, ST, P wave, Q wave, R wave, S wave, ST segment, T wave, U wave segments, for example) of the filtered sampled data signal.

In step 416, signal processor 15 uses the received sampled data in determining multiple first signal characteristic values over multiple heart cycles including, a first signal characteristic value substantially comprising a time interval between a peak of a P wave to a peak of a succeeding R wave representing a repolarization time interval in an individual heart cycle. Signal processor 15 uses a peak detector and time detector for identifying the peaks and detecting a time difference between the identified peaks. Processor 15 also calculates multiple first signal characteristic values including $T_D$, $T_R$, $T_{PQ}$ and $T_{QR}$ and associated ratios and the time-frequency parameters and parameters described in connection with the table of FIG. 4. The calculations are iteratively performed in step 416 for different portions of a single heart cycle and for multiple heart cycles for a region of interest (ROI) until the desired signal portion calculations are completed. Processor 15 in step 420 analyzes the multiple first signal characteristic values by performing a statistical analysis and calculating mean or average value, standard deviation, signal variation and signal variability as previously described.

In step 426 signal processor 15 employs mapping information, associating ranges of a calculated first signal characteristic value or values derived from the first signal characteristic value, with corresponding medical conditions (e.g., arrhythmias) in determining patient medical conditions, events and patient health status. If signal processor 15 and comparator 20 in step 426 determine a medical condition indicating cardiac impairment or another abnormality is identified, processor 15 in step 435 uses the mapping information in determining severity, type and location of a cardiac condition. Patient monitor 19 in step 437 generates an alert message identifying the medical condition and abnormality and communicates the message to a user and stores data indicating the identified condition and associated calculated parameters in repository 17. Processor 15 also determines the severity and location of the condition.

Processor 15 in step 423 selects a signal channel of a multi-channel catheter for use as signal input and adaptively adjusts the number of heart cycles in a calculation window used for averaging and adjusts the selected portions and ROI of a filtered signal analyzed and adjusts a threshold employed by comparator 20 to improve medical condition detection. In the atrial arrhythmia analysis, processor 15 selects a severity threshold, calculation time step, monitored tissue location in response to user command or automatic system adaptive adjustment. The multi-channel patient signals include different lead signals or surface ECG signals or different channels (unipolar or bipolar) ICEG signals. If signal processor 15 and comparator 20 in step 426 do not identify a medical condition, the process is repeated from step 408. System 10 identifies and monitors different kinds of clinical events and cardiac pathology, including atrial fibrillation and ventricular tachycardia using the calculated parameters and ratios.

Figure 7:
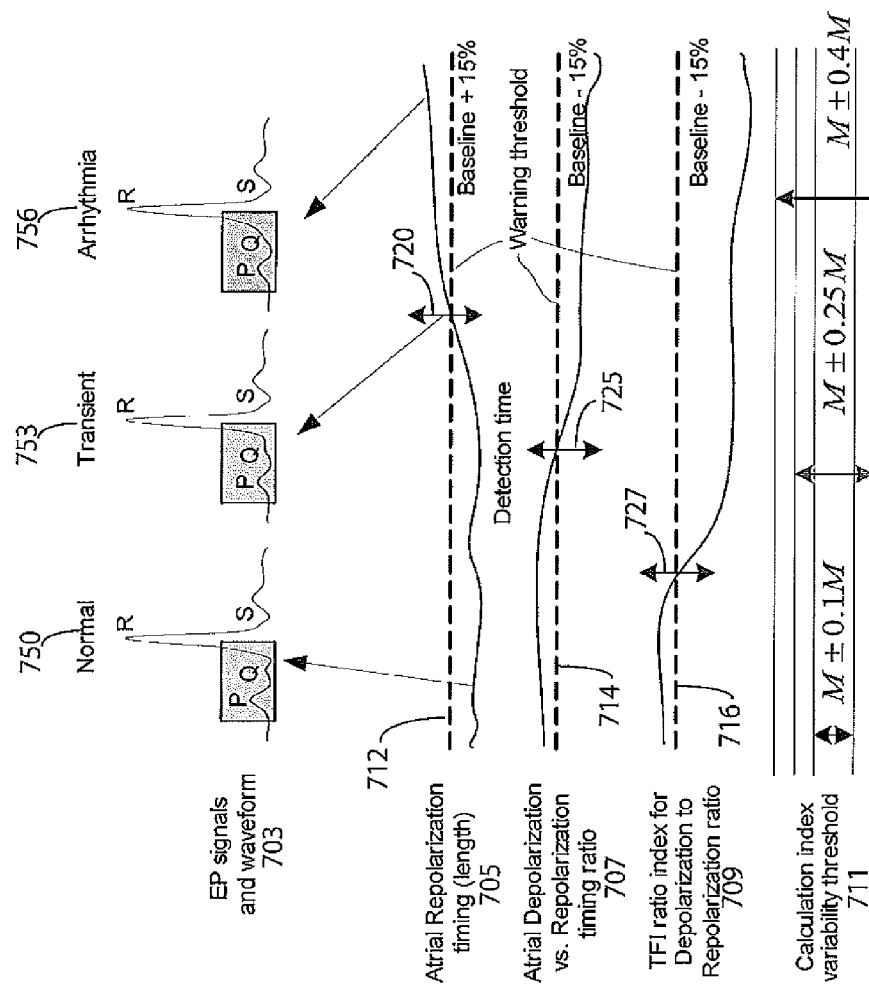
FIG. 7 shows atrial repolarization signal and activity analysis based on time domain and time-frequency domain analysis, according to invention principles.

FIG. 7 shows atrial repolarization signal and activity analysis based on time domain and time-frequency domain analysis. The atrial repolarization quantification and characterization analysis performed by system 10 (FIG. 1) is used to monitor and diagnose different kinds of clinical events and cardiac pathologies in an atrium, such as atrial fibrillation and atrial flutter. FIG. 7 shows an example, of simulated atrial fibrillation data analysis involving normal 750, transient 753 and atrial fibrillation (arrhythmia) 756 stages of an EP signal waveform 703. Processor 15 adaptively calculates and plots different types of parameter including, an atrial repolarization time duration $T_R$ parameter shown in plot 705, an atrial depolarization and repolarization time duration ratio $Ratio_{D-R}$ parameter shown in plot 707, an atrial depolarization and repolarization TFI ratio $TFI_{Atrial\_function\_ratio}$ parameter shown in plot 709.

System 10 determines abnormality at point 720 in the atrial repolarization waveform 705 in response to the waveform exceeding predetermined (+15% above baseline (normal) range) threshold 712. System 10 determines abnormality at point 725 in the atrial depolarization and repolarization time duration ratio waveform 707 in response to the waveform exceeding predetermined (−15% below baseline range) threshold 714. System 10 determines abnormality at point 727 in the atrial depolarization and repolarization TFI ratio waveform 709 in response to the waveform exceeding predetermined (−15% below baseline range) threshold 716. The calculated parameter thresholds 711 for the normal 750, transient 753 and atrial fibrillation (arrhythmia) 756 stages are shown as M+/−10%, M+/−25% and M+/−40%, respectively where M is a maximum value of a normalized baseline parameter of a healthy person. System 10 uses calculated parameter variability threshold (predetermined baseline and warning threshold) analysis to detect acute and small changes and associated trends within atrial signals.

System 10 adaptively selects the number of heart cycles used in a calculation window used for averaging to determine a mean and standard deviation value for calculated parameters, such as time duration and ratio parameters. Normal signals in the calculation are used as a reference (baseline) signal. The real time calculation continuously computes time duration value, and time-frequency calculated value. These calculated values are normalized with a reference signal so a calculated normal parameter value equals "1". If a real time calculated value (normalized) is higher or lower (such as 0.775 for depolarization to repolarization time duration ratio, e.g. due to atrial fibrillation) than the normal value "1", patient monitor 19 outputs a warning to a user and system 10 identifies a treatment such as ablation treatment in response to +/−15% variation from a normalized reference value, for example. The calculations are used together to characterize clinical patient atrial arrhythmias. The calculated parameters are used in combination to determine patient health status and pathology. Further, different methods are usable for multiple catheter channel analysis, such as a Fuzzy system or expert system, for example. In one embodiment an ANN (artificial neural network) is used for decision analysis for multiple catheter channel analysis and multiple parameter based patient monitoring.

Figure 8:
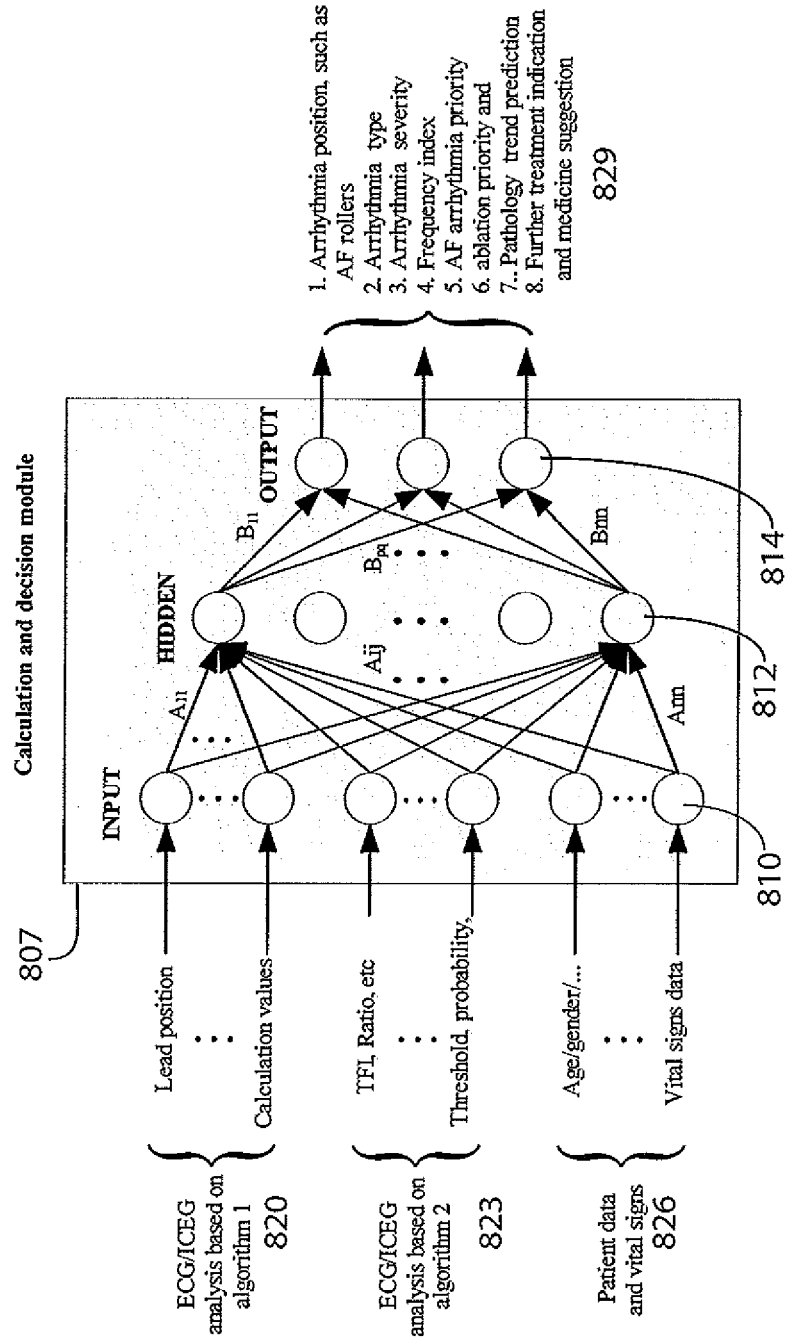
FIG. 8 shows an artificial neural network (ANN) used for atrial arrhythmia detection and heart function analysis, according to invention principles.

FIG. 8 shows an artificial neural network (ANN) system 807 used for atrial arrhythmia detection and heart function analysis. ANN unit 807 employs the calculated time duration and TFI parameters and patient vital sign signals to identify cardiac disorders. ANN unit 807 maps the calculated time duration parameters $T_D$, $T_R$, $T_{PQ}$ and $T_{QR}$ 820 and associated ratios and time-frequency parameters 823, as well as patient vital sign signals and demographic (age, gender, height, weight) data 826, to output parameters 829. Output parameters 829 include data indicating AF position, arrhythmia type and severity, an arrhythmia frequency indicator, an arrhythmia treatment urgency and priority of associated ablation tissue sites, a pathology trend indication and candidate treatment suggestions. ANN unit 807 structure comprises 3 layers, an input layer 810, hidden layer 812 and output layer 814. ANN unit $A_{ij}$ weights are applied between input layer 810 and hidden layer 812 components of the ANN computation and $B_{pq}$ weights are applied between hidden layer 812 and calculation index components 814 of the ANN computation. The $A_{ij}$ weights and $B_{pq}$ weights are adaptively adjusted and tuned using a training data set. ANN unit 807 incorporates a self-learning function that processes signals 820, 823 and 826 to increase the accuracy of calculated results. The ANN analysis of an atrial signal also uses data indicating patient medical history and physician experience (in the form of selection of a calculation mode, for example) which reduces the risk to patient heart tissue from over-pacing and tissue impairment. The system may be advantageously utilized in general patient monitoring and implantable cardiac devices for real time automatic analysis and detection of cardiac arrhythmias and abnormalities.

The system 10 calculation of time duration, ratio, TFI and associated deviation parameters supports monitoring and characterizing of small cardiac electrophysiological signal distortion and variation within an atrium. The calculation is usable in different clinical cardiac applications, such as in implantable cardiac devices, which may be equipped with several intra-cardiac leads.

Figure 9:
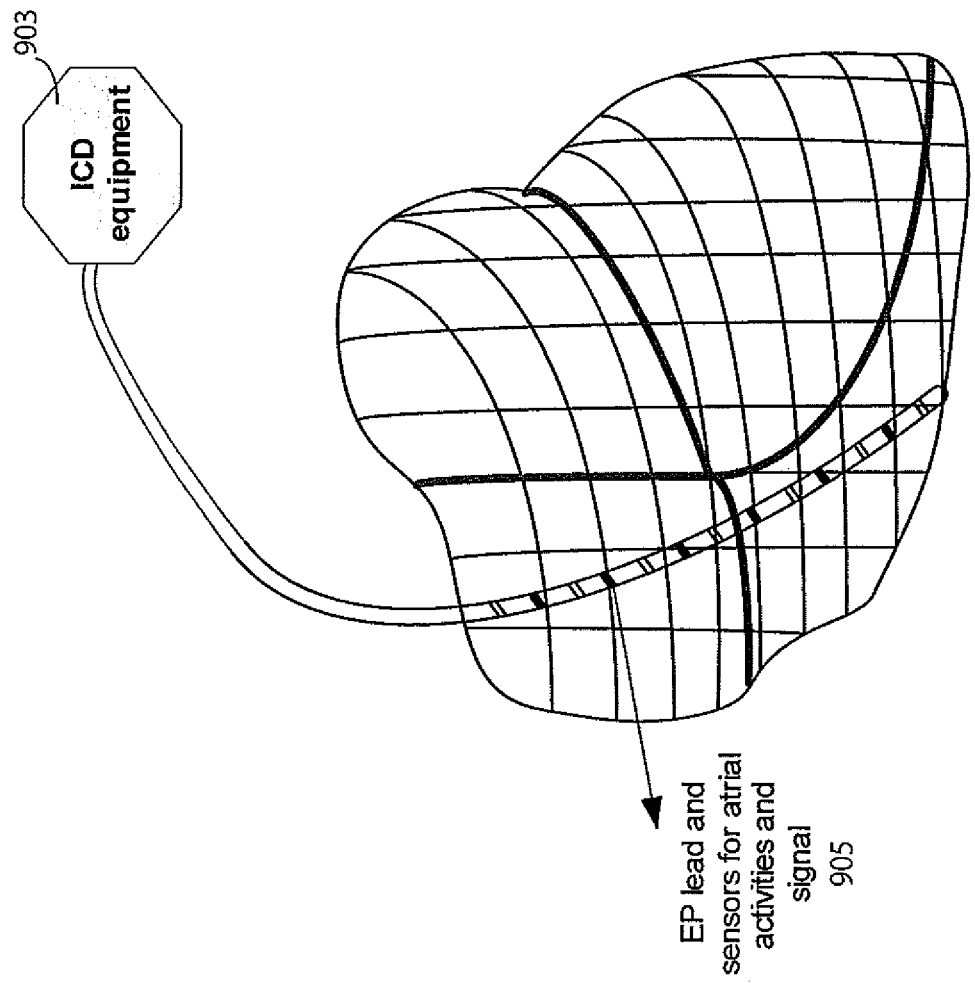
FIG. 9 shows an ICD system for atrial repolarization analysis, according to invention principles.

FIG. 9 shows an implantable cardioverter-defibrillator (ICD) system 903 for atrial repolarization analysis. ICD system 903 performs atrial depolarization and repolarization analysis as well as known intra-cardiac signal analysis. In ICD device 903, there are multi-channel sensors and transducers, which capture real time signals, such as EP, pressure signals from multiple different anatomical sites acquired by multi-channel catheter 905 (or multiple different catheters), for example. Additionally, the multiple-channel atrial repolarization calculations are performed in 2-dimensions and 3-dimensions for heart mapping. Furthermore, the multi-dimensional signal time duration and information ratio (atrial depolarization and repolarization) information mapping is used in real time cardiac function diagnosis. System 10 (FIG. 1) uses multi-channel atrial time duration and ratio distribution information mapping to locate abnormal tissue, a potential abnormal pathway and arrhythmia severity, in a visual cardiac representation to improve feedback to a user for use in identifying treatment.

Figure 10:
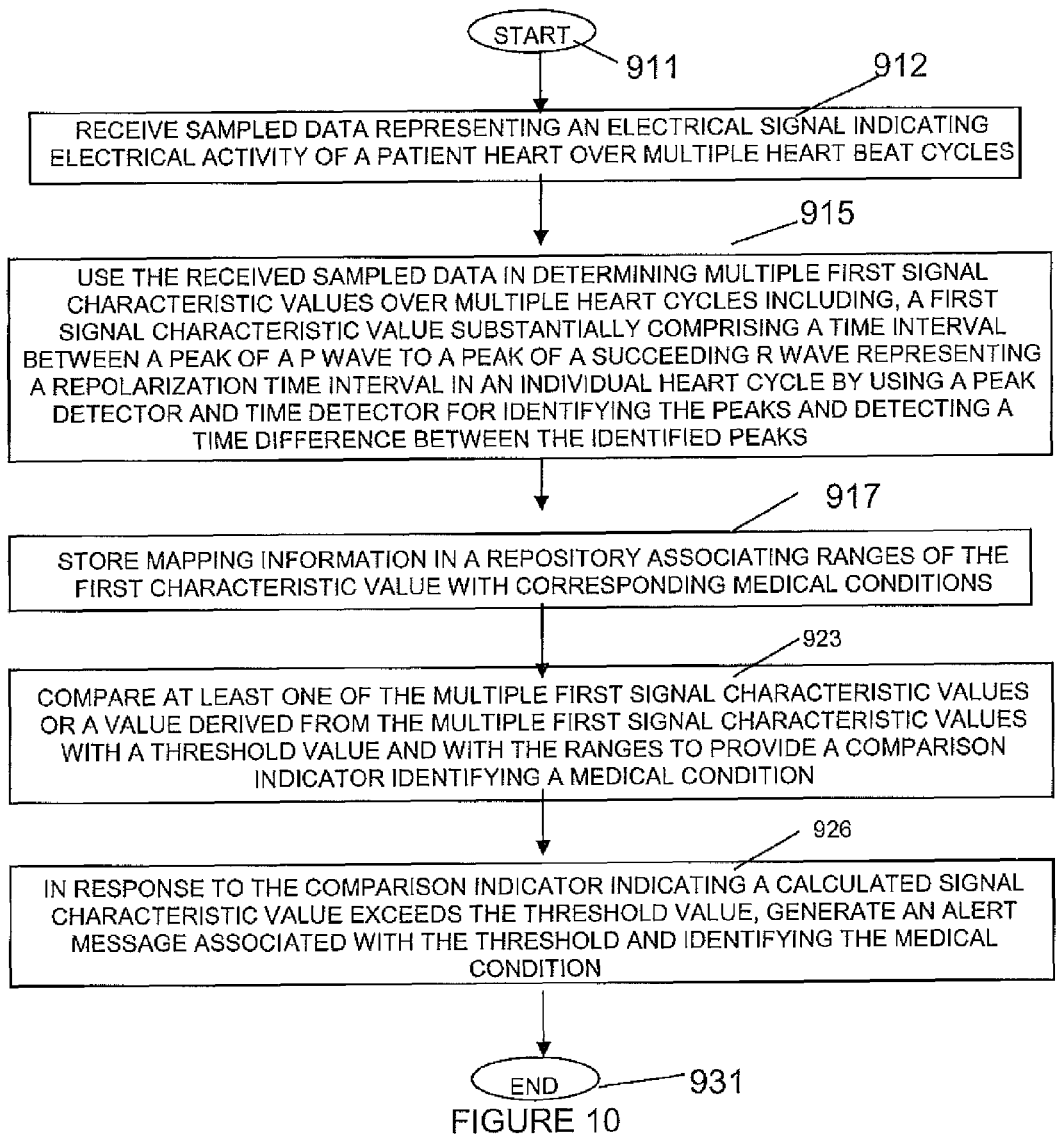
FIG. 10 shows a flowchart of a process used by a system for heart performance characterization and abnormality detection, according to invention principles.

FIG. 10 shows a flowchart of a process used by system 10 (FIG. 1) for heart performance characterization and abnormality detection. In step 912 following the start at step 911, interface 12 receives sampled data representing an electrical signal indicating electrical activity of a patient heart over multiple heart cycles comprising successive heart cycles. Signal processor 15 in step 915 uses the received sampled data in determining multiple first and second signal characteristic values over multiple heart cycles. A first signal characteristic value substantially comprises a time interval between a peak of a P wave to a peak of a succeeding R wave representing a repolarization time interval in an individual heart cycle. A second signal characteristic value substantially comprises a time interval between the start of a P wave to a peak of the P wave representing a depolarization time interval in an individual heart cycle. Signal processor 15 uses a peak detector and time detector for identifying the peaks and detecting a time difference between the identified peaks and uses a wave start detector and time detector for identifying the start and peak points of the P and R waves.

Signal processor 15 determines a ratio of a first signal characteristic value to a second signal characteristic value and a ratio of a value derived from multiple first signal characteristic values to a value derived from the multiple second signal characteristic values. Processor 15 determines a second signal characteristic value substantially comprising a time interval between a peak of a P wave to a peak of a succeeding Q wave in an individual heart cycle. Processor 15 uses a wave start and peak detector and time detector for identifying the start and peak points of the Q wave and P wave and for detecting a time difference between the identified points. Signal processor 15 also determines a second signal characteristic value substantially comprising a time interval between a peak of a Q wave to an R wave peak in an individual heart cycle and processor 15 uses a wave start and peak detector and time detector for identifying the start and peak points of the Q wave and R wave and for detecting a time difference between the identified points.

Processor 15 determines a second signal characteristic value substantially comprising an integral of a time-frequency product over a time interval between a peak of a P wave to a peak of a succeeding R wave representing a repolarization time interval. Processor 15 uses the received sampled data in determining multiple third signal characteristic values over multiple heart cycles. A third signal characteristic value substantially comprises an integral of a time-frequency product over a time interval between the start of a P wave to a peak of the P wave representing a depolarization time interval and processor 15 calculates a ratio of a second signal characteristic value to a third characteristic value.

Signal processor 15 employs a heart cycle synchronization signal in determining multiple first signal characteristic values over the multiple heart cycles and provides the value derived from the multiple first signal characteristic values by averaging the multiple first signal characteristic values over the multiple heart cycles. Further, signal processor 15 provides the value derived from the multiple first signal characteristic values by determining a standard deviation or variance of the multiple first signal characteristic values over the multiple heart cycles. Also in one embodiment processor 15 provides the value derived from the multiple first signal characteristic values by determining a ratio of an average of the multiple first signal characteristic values to a standard deviation or variance of the multiple first signal characteristic values.

In step 917, processor 917 stores in repository 17, mapping information, associating ranges of the first characteristic value with corresponding medical conditions. The predetermined mapping information associates ranges of the first and second characteristic values with particular patient demographic characteristics and with corresponding medical conditions and the system uses patient demographic data including at least one of age weight, gender and height in comparing the first and second characteristic values with the ranges and generating an alert message indicating a potential medical condition. Comparator 20 in step 923 compares at least one of the multiple first and second signal characteristic values or a value derived from the multiple first and second signal characteristic values with a threshold value and with the ranges to provide a comparison indicator identifying a medical condition.

Comparator 20 also determines a comparison indicator indicating whether the at least one of the first and second signal characteristic values lies in a predetermined value range. The threshold value is derived from recorded electrical signal data for the patient or for a population of patients and signal processor 15 dynamically adjusts at least one of the predetermined threshold values in response to a determined sensitivity of arrhythmia detection or determined heart electrical activity signal variation of the patient. The population of patients has similar demographic characteristics including at least two of, (a) age, (b) weight, (c) gender and (d) height, to those of the patient. In step 926, patient monitor 19, in response to the comparison indicator indicating a calculated signal characteristic value exceeds the threshold value or lies in a predetermined value range or outside of a range, generates an alert message associated with the threshold and identifying the medical condition. The process of FIG. 10 terminates at step 931.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-10 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system analyzes atrial depolarization and repolarization activity, involving a P wave, PQ wave and QR wave, for example, to provide an accurate time and severity of atrial pathologies and events for improved diagnosis, such as of AF arrhythmia. Further, the processes and applications may, in alternative embodiments, be located on one or more (e.g., distributed) processing devices on a network linking the units of FIG. 1. Any of the functions and steps provided in FIGS. 1-10 may be implemented in hardware, software or a combination of both.

What is claimed is:

1. A system for heart performance characterization and abnormality detection, comprising:
   an interface for receiving sampled data representing an electrical signal indicating electrical activity of a patient heart over a plurality of heart beat cycles;
   a signal processor including a peak detector and time detector for identifying peaks and detecting a time difference between the identified peaks of the received sampled data, said signal processor being configured to process the received sampled data in determining,
      a plurality of first signal characteristic values over a plurality of heart cycles including, a first signal characteristic value comprising a time interval between a peak of a P wave to a peak of a succeeding R wave representing a repolarization time interval in an individual heart cycle and
      a plurality of second signal characteristic values over a plurality of heart cycles, a second signal characteristic value comprising a time interval between the start of a P wave to a peak of the P wave representing a depolarization time interval in an individual heart cycle;
   a comparator for comparing at least one of the plurality of first and second signal characteristic values or a value determined by said signal processor from both the first and the second signal characteristic value, with a threshold value to provide a comparison indicator; and
   a patient monitor for generating an alert message associated with the threshold in response to said comparison indicator.

2. A system according to claim 1, wherein
said value determined from both said first and second signal characteristic value comprises at least one of, a ratio, a ratio mean, a ratio standard deviation and a ratio variance.

3. A system according to claim 1, wherein
said signal processor derives a value from one or more of said plurality of first signal characteristic values and said signal processor determines a ratio of a value derived from said plurality of first signal characteristic values to a value derived from said plurality of second signal characteristic values.

4. A system according to claim 1, wherein
said plurality of second signal characteristic values further comprises a time interval between a peak of a P wave to a peak of a succeeding Q wave in an individual heart cycle and said signal processor uses the peak detector and the time detector for identifying the start and peak points of the Q wave and P wave and for detecting a time difference between the identified points.

5. A system according to claim 1, wherein
said plurality of second signal characteristic values further comprises a time interval between a peak of a Q wave to an R wave peak in an individual heart cycle and said signal processor uses a wave start and peak detector and time detector for identifying the start and peak points of the Q wave and R wave and for detecting a time difference between the identified points.

6. A system according to claim 1, wherein
said plurality of second signal characteristic values further comprises an integral of a time-frequency product over a time interval between a peak of a P wave to a peak of a succeeding R wave representing a repolarization time interval.

7. A system according to claim 6, wherein
said signal processor is configured to use the received sampled data in determining a plurality of third signal characteristic values over a plurality of heart cycles, a third signal characteristic value substantially comprising an integral of a time-frequency product over a time interval between the start of a P wave to a peak of the P wave representing a depolarization time interval.

8. A system according to claim 7, wherein
said signal processor calculates a ratio of a second signal characteristic value to the third characteristic value.

9. A system according to claim 1, wherein
said signal processor is adapted to determine said plurality of first signal characteristic values over said plurality of heart cycles in response to synchronization with a heart cycle synchronization signal.

10. A system according to claim 1, wherein
said signal processor derives a value from one or more of said plurality of first signal characteristic values and
said signal processor provides said value derived from said plurality of first signal characteristic values by averaging said plurality of first signal characteristic values over said plurality of heart cycles.

11. A system according to claim 1, wherein
said signal processor derives a value from one or more of said plurality of first signal characteristic values and
said signal processor provides said value derived from said plurality of first signal characteristic values by determining a standard deviation or variance of said plurality of first signal characteristic values over said plurality of heart cycles.

12. A system according to claim 1, wherein
said signal processor derives a value from one or more of said plurality of first signal characteristic values and
said signal processor provides said value derived from said plurality of first signal characteristic values by determining a ratio of an average of said plurality of first signal characteristic values to a standard deviation or variance of said plurality of first signal characteristic values.

13. A system according to claim 1, including
a repository of mapping information, associating ranges of said first characteristic value with corresponding medical conditions and
said comparator compares said first characteristic values with said ranges to provide a comparison indicator identifying a medical condition and
said patient monitor generates an alert message identifying said medical condition.

14. A system according to claim 13, wherein
said predetermined mapping information associates ranges of said first characteristic values with particular patient demographic characteristics and with corresponding medical conditions and said system is configured to use patient demographic data including at least one of, age weight, gender and height in comparing said first characteristic value with said ranges and generating an alert message indicating a potential medical condition.

15. A system according to claim 1, including
a repository of mapping information, associating ranges of said first and second characteristic values with corresponding medical conditions and
said comparator compares said first and second characteristic values with said ranges to provide a comparison indicator identifying a medical condition and
said patient monitor generates an alert message identifying said medical condition.

16. A system according to claim 15, wherein
said predetermined mapping information associates ranges of said first and second characteristic values with particular patient demographic characteristics and with corresponding medical conditions and said system is configured to use patient demographic data including at least one of, age weight, gender and height in comparing the first and second characteristic values with said ranges and generating an alert message indicating a potential medical condition.

17. A system for heart performance characterization and abnormality detection, comprising:
an interface for receiving sampled data representing an electrical signal indicating electrical activity of a patient heart over a plurality of heart beat cycles;
a signal processor including a peak detector and time detector for identifying peaks and detecting a time difference between the identified peaks of the received sampled data, said signal processor being configured to process the received sampled data in determining,
a plurality of first signal characteristic values over a plurality of heart cycles including, a first signal characteristic value comprising a time interval between a peak of a P wave to a peak of a succeeding R wave representing a repolarization time interval in an individual heart cycle and
a plurality of second signal characteristic values over a plurality of heart cycles, a second signal characteristic value comprising a time interval between the start of a P wave to a peak of the P wave representing a depolarization time interval in an individual heart cycle;
a comparator for comparing a ratio determined by said signal processor from both the first and the second signal characteristic value, with a threshold value to provide a comparison indicator; and
a patient monitor for in response to said comparison indicator indicating at least one of said plurality of first signal characteristic values exceeds the threshold value, generating an alert message associated with the threshold.

18. A system for heart performance characterization and abnormality detection, comprising:
an interface for receiving sampled data representing an electrical signal indicating electrical activity of a patient heart over a plurality of heart beat cycles;
a signal processor configured to use the received sampled data in determining a plurality of first and second signal characteristic values over a plurality of heart cycles including,
a first signal characteristic value comprising a time interval between a peak of a P wave to a peak of a succeeding R wave representing a repolarization time interval in an individual heart cycle and
a second signal characteristic value comprising a time interval between the start of a P wave to a peak of the P wave representing a depolarization time interval in an individual heart cycle and said signal processor identifies the start and peak points of the P and R waves and detects a time difference between the identified points and
derives a value from at least one of the first and second signal characteristic value;
a comparator for comparing at least one of,
a value determined by said signal processor from both the first and the second signal characteristic value, with a threshold value to provide a comparison indicator,
the plurality of first signal characteristic values or a value derived from said plurality of first signal characteristic values with a threshold value to provide a comparison indicator and
the plurality of second signal characteristic values or a value derived from said plurality of second signal characteristic values with a threshold value to provide a comparison indicator; and
a patient monitor for generating an alert message associated with the threshold in response to a comparison indicator provided by said comparator.

19. A system according to claim 18, wherein
said comparator determines a comparison indicator indicating whether said at least one of the first and second signal characteristic values lies in a predetermined value range and
said patient monitor, in response to a comparison indicator provided by said comparator indicating the first or second calculated signal characteristic value lies in a predetermined value range, generates an alert message associated with the value range.

20. A system according to claim 18, wherein
said signal processor derives said threshold value from recorded electrical signal data for said patient.

21. A system according to claim 18, wherein
said signal processor derives said threshold value from recorded electrical signal data for a population of patients.

22. A system according to claim 21, wherein
said population of patients has similar demographic characteristics including at least two of, (a) age, (b) weight, (c) gender and (d) height, to those of said patient.

23. A system according to claim 18, wherein
said signal processor dynamically adjusts said threshold value in response to heart electrical activity signal variation of the patient.

24. A system according to claim 18, wherein said plurality of heart cycles are successive heart cycles.

25. A system according to claim 18, wherein said signal processor dynamically adjusts at least one of the threshold values in response to heart electrical activity signal variation of said patient.

26. A method for heart performance characterization and abnormality detection, comprising the activities of:
  receiving sampled data representing an electrical signal indicating electrical activity of a patient heart over a plurality of heart beat cycles;
  using a peak detector and time detector for identifying the peaks and detecting a time difference between the identified peaks;
  using the received sampled data and identified peaks and detected time difference in determining,
    a plurality of first signal characteristic values over a plurality of heart cycles including, a first signal characteristic value comprising a time interval between a peak of a P wave to a peak of a succeeding R wave representing a repolarization time interval in an individual heart cycle and
    a plurality of second signal characteristic values over a plurality of heart cycles, a second signal characteristic value comprising a time interval between the start of a P wave to a peak of the P wave representing a depolarization time interval in an individual heart cycle;
  comparing at least one of the plurality of first and second signal characteristic values or a determined from both the first and the second signal characteristic value, with a threshold value to provide a comparison indicator; and
  generating an alert message associated with the threshold in response to said comparison indicator.

* * * * *